US008598126B2

(12) United States Patent
Hoppe-Seyler et al.

(10) Patent No.: US 8,598,126 B2
(45) Date of Patent: Dec. 3, 2013

(54) PEPTIDES FOR INHIBITING THE HPV-E6 ONCOPROTEIN

(75) Inventors: Felix Hoppe-Seyler, Hirschberg (DE); Karin Hoppe-Seyler, Hirschberg (DE); Susanne Kintscher, Teterew (DE)

(73) Assignee: DKFZ Deutsches Krebsforschungszentrum, Stiftung des offentlichen Rechts, Heidelberg (DE)

( * ) Notice: Subject to any disclaimer, the term of this patent is extended or adjusted under 35 U.S.C. 154(b) by 282 days.

(21) Appl. No.: 12/936,679

(22) PCT Filed: Apr. 7, 2009

(86) PCT No.: PCT/EP2009/054143
§ 371 (c)(1),
(2), (4) Date: Jan. 5, 2011

(87) PCT Pub. No.: WO2009/124932
PCT Pub. Date: Oct. 15, 2009

(65) Prior Publication Data
US 2011/0201560 A1    Aug. 18, 2011

(30) Foreign Application Priority Data

Apr. 8, 2008   (EP) .................................... 08154215

(51) Int. Cl.
| | | |
|---|---|---|
| *A61K 38/00* | (2006.01) | |
| *A61P 35/00* | (2006.01) | |
| *C07K 5/00* | (2006.01) | |
| *C07K 7/00* | (2006.01) | |
| *C07K 16/00* | (2006.01) | |
| *C07K 17/00* | (2006.01) | |
| *A61K 38/04* | (2006.01) | |
| *C12N 15/00* | (2006.01) | |
| *C12N 1/00* | (2006.01) | |
| *C12N 5/04* | (2006.01) | |
| *C12N 5/10* | (2006.01) | |
| *C12N 5/02* | (2006.01) | |

(52) U.S. Cl.
USPC ........ 514/19.3; 514/19.2; 514/44 R; 530/324; 530/325; 530/326; 530/327; 530/328; 435/320.1; 435/243; 435/419; 435/325

(58) Field of Classification Search
None
See application file for complete search history.

(56) References Cited

U.S. PATENT DOCUMENTS

| | | | |
|---|---|---|---|
| 5,532,348 | A | 7/1996 | Huibregtse et al. |
| 5,821,051 | A | 10/1998 | Androphy et al. |
| 5,858,987 | A | 1/1999 | Beer-Romero et al. |
| 5,914,389 | A | 6/1999 | Huibregtse et al. |
| 5,989,804 | A | 11/1999 | Androphy et al. |
| 6,296,853 | B1 | 10/2001 | Androphy et al. |
| 6,610,473 | B1 | 8/2003 | Butz et al. |
| 6,703,491 | B1 * | 3/2004 | Homburger et al. ......... 536/23.1 |
| 2003/0194704 | A1 * | 10/2003 | Penn et al. ....................... 435/6 |

FOREIGN PATENT DOCUMENTS

| | | |
|---|---|---|
| DE | 199 01 008 A1 | 7/2000 |
| EP | 0 531 080 A2 | 3/1993 |
| WO | WO 96/40767 | 12/1996 |
| WO | WO 97/18236 | 5/1997 |
| WO | WO 00/42064 | 7/2000 |
| WO | WO 01/87953 * 11/2001 ........... C07K 14/435 |

OTHER PUBLICATIONS

Hirsch-Behnam et al. A comparative sequence analysis of two human papillomavirus (HPV) types 2a and 57, Virus Research, 1990, vol. 18, Issue 1, pp. 81-98.*
English translation of WO2001/087953, Publication date Nov. 22, 2001, 39 pages.*
Akgul et al., "HPV-associated skin disease," *Journ. of Pathology*, pp. 165-175 (2006).
Allen et al., "A Plant Lignan, 3'-O-Methyl-Nordihydroguaiaretic Acid, Suppresses Papillomavirus E6 Protein Function, Stabilizes p53 Protein, and Induces Apoptosis in Cervical Tumor Cells," *Molecular Carcinogenesis*, vol. 46, pp. 564-575 (2007).
Baleja et al., "Identification of Inhibitors to Papillomavirus type 16 E6 protein based on three-dimensional structures of interacting proteins," *Antiviral Research*, vol. 72, pp. 49-59 (2006).
Be et al., "Solution Structure Determination and Mutational Analysis of the Papillomavirus E6 Interacting Peptide of E6AP," *Biochemistry*, vol. 40, pp. 1293-1299 (2001).
Bosch et al., "Prevalence of Human Papillomavirus in Cervical Cancer: A Worldwide Perspective," *Journ. of the National Cancer Inst.*, vol. 87, No. 11, pp. 796-802 (1995).
Butz et al., "Transcriptional Countrol of Human Papillomavirus (HPV) Oncogene Expression: Composition of the HPV Type 18 Upstream Regulatory Region," *Journ. of Virology*, pp. 6476-6486 (1993).
Butz et al., "Induction of Apoptosis in Human Papillomavirus-Positive Cancer Cells by Peptide Aptamers Targeting the Viral E6 Oncoprotein," *PNAS*, vol. 97, No. 12, pp. 6693-6697 (2000).
Butz et al., "siRNA Targeting of the Viral E6 Oncogene Efficiently Kills Human Papillomavirus-positive Cancer Cells," *Oncogene*, pp. 5938-5945 (2003).
Chen et al., "Interaction of Papillomavirus E6 Oncoproteins with a Putative Calcium-Binding Protein," *Science*, vol. 269, p. 529-531 (1995).

(Continued)

*Primary Examiner* — Marcela M Cordero Garcia
(74) *Attorney, Agent, or Firm* — Foley & Lardner LLP

(57) ABSTRACT

The present invention is concerned with means and methods for diagnosing or treating HPV associated neoplasia or tumors. Specifically, it relates to a peptide comprising an amino acid sequence motif as shown in SEQ ID No: 1. Moreover, contemplated by the present invention are fusion polypeptides, polynucleotides, vectors and host cells based on said peptide. Furthermore, the peptides, fusion polypeptides, polynucleotides, and vectors are suitable as pharmaceutical compositions for treating HPV associated neoplasia or tumors. The peptides and fusion polypeptides are also suitable as diagnostic compositions for diagnosing HPV associated neoplasia or tumors. The present invention also refers to a method of identifying a compound capable of binding to the HPV E6 protein. Finally, a kit is provided for carrying out the aforementioned diagnosis or compound identification.

19 Claims, 5 Drawing Sheets

(56) References Cited

OTHER PUBLICATIONS

Figure 2:
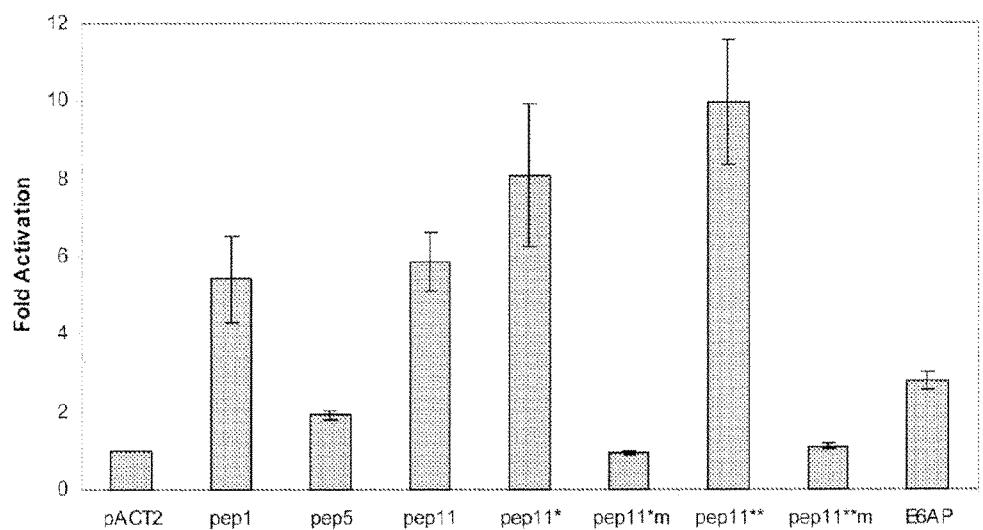

Chen et al., "Identification of an α Helical Motif Sufficient for Association with Papillomavirus E6," *The Journ. of Biol. Chemistry*, vol. 273, No. 22, pp. 13537-13544 (1998).
Dunne et al., "Genital Human Papillomavirus Infection," *Emerging Infections*, pp. 624-629 (2006).
Elston et al., "The Identification of a Conserved Binding Motif within Human Papillomavirus Type 16 E6 Binding Peptides, E6AP and E6BP," *Journ. of General Virology*, vol. 79, pp. 371-374 (1998).
Feng et al., "Progressive Sequence Alignment as a Prerequisite to Correct Phylogenetic Trees," *J. Mol. Evol.*, vol. 25, pp. 351-360 (1987).
Griffin et al., "Inhibition of Papillomavirus Protein Function in Cervical Cancer Cells by Intrabody Targeting," *J. Mol. Biol.*, vol. 355, pp. 360-378 (2006).
Higgins et al., "Fast and Sensitive Multiple Sequence Alignments on a Microcomputer," *Cabios Communications*, vol. 5, No. 2, pp. 151-153 (1989).
Hopp et al., "Prediction of Protein Antigenic Determinants form Amino Acid Sequences," *Proc. Natl. Acad. Sci.*, vol. 78, No. 6, pp. 3824-3828 (1981).
Hoppe-Seyler et al., "Peptide Aptamers: New Tools to Study Protein Interactions," *Journ. of Seroid Biochemistry & Molecular Biology*, vol. 78, pp. 105-111 (2001).
Hoppe-Seyler et al., "Peptide Aptamers: Specific Inhibitors of Protein Function," *Current Molecular Medicine*, vol. 4, pp. 529-538 (2004).
Huibregtse et al., "A Cellular Protein Mediates Association of p53 with the E6 Oncoprotein of Human Papillomavirus Types 16 or 18," *The EMBO Journ.*, vol. 10, No. 13, pp. 4129-4135 (1991).
Klevenz et al., "Peptide aptamers: exchange of the thioredoxin-A scaffold by alternative platform proteins and its influence on target protein binding," *CMLS, Cell. Mol. Life Sci.*, vol. 59, pp. 1993-1998 (2002).
Liu et al., Design and Characterization of Helical Peptides that Inhibit the E6 Protein of Papillomavirus, *Biochemistry*, vol. 43, pp. 7421-7431 (2004).
Lu et al., "Human Papillomavirus 16 E6 Oncoprotein Interferences with Insulin Signaling Pathway by Binding to Tuberin," *The Journ. of Biol. Chem.*, vol. 279, No. 34, pp. 35664-35670 (2004).
Psyrri et al., "Human Papillomavirus in Cervical and Head-and-Neck Cancer," *Nature Clin. Prac. Oncology*, vol. 5, No. 1, pp. 24-31 (2008).
Smith et al., "Comparison of Biosequences," *Advances in Applied Mathematics 2*, vol. 482-489 (1981).
Snyder et al., "Cell Penetrating Peptides in Drug Delivery," *Pharm. Research*, vol. 21, No. 3, pp. 389-393 (2004).
Tong et al., "The Bovine Papillomavirus E6 Protein Binds to the LD Motif Repeats of Paxillin and Blocks Its Interaction with Vinculin and the Focal Adhesion Kinase," *The Journ. of Biological Chem.*, vol. 272, No. 52, pp. 33373-33376 (1997).
Vidal et al., "Reverse two-hybrid and one-hybrid systems to detect dissociation of protein-protein and DNA-protein interactions," *Proc. Natl. Acad. Sci.*, vol. 93, pp. 10315-10320 (1996).
Vogt et al., "Inhibition of Bax Activity is Crucial for the Antiapoptotic Function of the Human Papillomavirus E6 Oncoprotein," *Oncogene*, vol. 25, pp. 4009-4015 (2006).
Walboomers et al., "Human Papillomavirus is a Necessary Cause of Invasive Cervical Cancer Worldwide," *Journ. of Pathology*, vol. 189, pp. 12-19 (1999).
Walensky et al., "Activation of Apoptosis in Vivo by a Hydrocarbon-Stapled BH3 Helix," *Science*, vol. 305, pp. 1466-1470 (2004).
Walensky et al., Supplemental Material, Experimental Procedures, "Synthesis of Stabilized Alpha-Helix of BCL-2 Domain (SAHB) Compounds," Supporting Online Material, 12 sheets plus Figs. S1-S3 (2004).
Zur Hausen, "Papillomaviruses and Cancer: from Basic Studies to Clinical Application," *Nature*, vol. 2, pp. 342-350 (2002).
The 20 Amino Acids: Hydrophobic, Hydrophilic, Polar and Charged Amino Acids and their Function in Protein Structures, http://www.proteinstructures.com/Structure/Structure/amino-acids.html, Aug. 23, 2011, p. 3-4.
European Office Communication dated Aug. 29, 2011, cited in related European Patent Application No. 09731344.9.
Dymalla et al., "A novel peptide motif binding to and blocking the intracellular activity of the human papillomavirus E6 oncoprotein," *J. Mol. Med.*, vol. 87, pp. 321-331 (2009).

* cited by examiner

Fig. 1 a)

a1:     NH₂ - KGSLNCSCLVCWLQMFLGEFGP- COOH
a2:     NH₂ - PFLLGCFCLCCWIECQIGSYGP- COOH
a3:     NH₂ - EFGSGCSCIVCIGLI- COOH
a4:     NH₂ - EYNSNCSCIACIGLI- COOH
a5:     NH₂ -KEKEEYNSNCSCIACIGLI- COOH b)

b1:     NH₂ - EYNSNSSSIASIGLI- COOH
b2:     NH₂ -KEKEEYNSNSSSIASIGLI- COOH c)

C - x - C - h - x - C – h – x - x – x d)

L - b - x - h - L - s – a

A

B

PEPTIDES FOR INHIBITING THE HPV-E6 ONCOPROTEIN

The present invention is concerned with means and methods for diagnosing or treating HPV associated neoplasia or tumors. Specifically, it relates to a peptide comprising an amino acid sequence motif as shown in SEQ ID No: 1. Moreover, contemplated by the present invention are fusion polypeptides, polynucleotides, vectors and host cells based on said peptide. Furthermore, the peptides, fusion polypeptides, polynucleotides, and vectors are suitable as pharmaceutical compositions for treating HPV associated neoplasia or tumors. The peptides and fusion polypeptides are also suitable as diagnostic compositions for diagnosing HPV associated neoplasia or tumors. The present invention also refers to a method of identifying a compound capable of binding to the HPV E6 protein. Finally, a kit is provided for carrying out the aforementioned diagnosis or compound identification.

Human papilloma viruses (HPVs) are responsible for carcinogenesis of various tumors. In particular, they are involved in cervical neoplasia or tumor formation. In 99% or more of all cervical tumor biopsies, oncogenic, high risk HPV types could be determined. DNA of high risk HPV types could be determined for HPV 16 in 50% of the investigated cases (Bosch 1995, J Natl Cancer Inst 87(11): 796-802; Walboomers 1999, J pathol 189(1): 12-19).

Moreover, HPVs are also reported in the formation of anogenital warts (*Condylomata acuminata*, *Condylomata plana*, *Condylomata gigantea* (Buschke-Loewenstein tumor)), Cervical Intraepithelial Neoplasia, *Bowenoid papulosis* (*Bowenoid dysplasia*, viral keratosis), mucosa warts, larynx papilloma, malignant tumors, preferably, spinalioma accompanied with *Epidermodysplasia verruciformis*, Morbus Bowen of the skin, penis carcinoma, vulva carcinoma, squamous cell carcinoma of the skin, cervical carcinoma, larynx carcinoma, tonsillar carcinoma, oropharynx or tongue carcinoma (Akgul 2006, J Pathol 208(2): 165-75, Dunne 2006, Clin Infect Dis 43(5): 624-9, Psyrri 2008, Nat Clin Pract Oncol 5(1): 24-31).

Two viral oncoproteins, HPV E6 and E7, have been identified to be involved in tumor progression. Both proteins are regularly expressed in HPV-positive cells and are necessary and sufficient to maintain their transformed phenotype. E7 is known to degrade the tumor suppressor pRb and related pocket proteins which are involved in control of cell cycle progression. This releases the pRb-dependent control of the E2F transcription factor, thereby promoting cell cycle progression. One important function of the E6 oncoprotein is the degradation of the p53 tumor suppressor, thereby blocking the anti-apoptotic activities of p53 (Zur Hausen 2002, Nat Rev Cancer 2(5): 342-50).

Recently, vaccines have been made available which shall prevent infection by high risk types HPV 16 and 18. Vaccination is, however, only effective for subjects which have not already been infected by HPVs. For patients suffering already from the aforementioned diseases caused by HPVs, surgery in combination with radiation therapy or chemotherapy is applied as the standard therapeutic measure. These therapeutic measures, of course, are rather unspecific and/or have severe side effects.

Experimental approaches have been reported which aim to inhibit the HPV E6 on either protein or RNA level; see Butz 2000, Proc Natl Acad Sci USA. 97(12):6693-7, Butz 2003, Oncogene 22(38):5938-45, Hoppe-Seyler 2004, Curr Mol. Med. 4(5):529-38, Vogt 2006, Oncogene 25(29):4009-15, Allen 2007, Mol. Carcinog. 46(7):564-75, Griffin 2006, Mol. Biol. 355(3):360-78, Baleja 2006, Antiviral Res. 72(1):49-59, Liu 2004, Biochemistry 43(23):7421-31, DE 199 01 008 A1, U.S. Pat. No. 5,914,389, U.S. Pat. No. 5,532,348, U.S. Pat. No. 6,296,853, U.S. Pat. No. 5,989,804, U.S. Pat. No. 5,821,051, U.S. Ser. No. 08/273,059, WO 96/40767, U.S. Pat. No. 5,858,987, EP 0 531 080 A2, and WO 00/42064.

However, therapies which specifically affect HPV infected tumors or neoplasia are still highly desirable.

In order to meet this desire, peptide aptamers inhibiting HPV E6 in particular have received wide interest (see references above). Most screening systems for the identification of peptide aptamers rely on the use of fusion proteins consisting of candidate peptides fused into "scaffold" proteins which stabilize the candidate peptides. It was, however, realized, that these scaffold proteins also provide a conformational restraint which in most cases is required for the peptides to bind to their target(s). In effect, in the case of HPV E6 such screenings led to the identification of candidate peptides, of which almost all only recognize the respective targets in the context of the specific screening system used or which have no in vitro binding capacity (Butz 2000, Proc Natl Acad Sci USA. 97(12):6693-7, WO 00/42064). As a further consequence, peptides identified in conventional screening systems often lose their binding properties, and hence their activity, if they are used in the context of a different scaffold protein or as free peptides (e.g. Klevenz et al. 2002, Cell Mol Life Sci 59, 1993-1998), so there still is a need for peptide aptamers that retain HPV E6 binding activity, and thus inhibitory activity, independently of the fusion partner used or when used as free peptides.

The technical problem underlying the present invention, thus, could be seen as the provision of means and methods for complying with the aforementioned needs. The said technical problem is solved by the embodiments characterized in the claims and herein below.

Thus, the present invention relates to a peptide comprising an amino acid sequence motif as shown in SEQ ID No: 1.

The term "peptide" as used herein refers to small amino acid chains of between 7 to 50 amino acids in length comprising the sequence motif shown in SEQ ID NO: 1, i.e. the following contiguous amino acids:

C-x-C-h-x-C-h-x-x-x, wherein x is any amino acid, and preferably, a naturally occurring amino acid, and wherein h is a hydrophobic amino acid, preferably W, I, L or V. Amino acids are referred to in the so called "One-Letter-Code". A hydrophobic amino acid in accordance with the present invention has a hydrophobicity according to the Hopp-Woods Scale of less than −0.5 (e.g., −0.6, −0.7, −0.8 etc.). How to determine the hydrophobicity (or sometimes referred to as hydrophilicity) according to Hopp-Woods is well known in the art and disclosed in standard text books (see also Hopp 1981, Proc Natl Acad Sci USA 78:3824, 1981).

Preferably, the said peptide essentially consists of no more than 30 amino acids, i.e. between 7 and 30 amino acids. Most preferably, it essentially consists of 15 to 19 amino acids in length. Preferably, said peptide comprises or essentially consists of an amino acid sequence as shown in any one of SEQ ID Nos: 2 to 6. Further, peptides of the present invention include variants of any one of SEQ ID Nos: 2 to 6, wherein said variants have an amino acid sequence being at least 70%, at least 80%, at least 90%, at least 95%, least 96%, at least 97%, at least 98% or at least 99% identical to the amino acid sequence shown in any one of SEQ ID Nos: 2 to 6 provided, however, that the said variant comprises the sequence motif referred to above and shown in SEQ ID NO: 1. The degree of identity between two given sequences (amino acids or nucleic acids) can be determined, preferably, by the algorithms of Needleman and Wunsch or Smith and Waterman. To carry out the sequence alignments, the program PileUp (J. Mol. Evolution., 25, 351-360, 1987, Higgins et al., CABIOS, 5 1989: 151-153) or the programs Gap and BestFit (Needleman 1970, J. Mol. Biol. 48; 443-453 and Smith 1981, Adv. Appl. Math. 2; 482-489), which are part of the GCG software packet (Genetics Computer Group, 575 Science Drive, Madison, Wis., USA 53711, Version 1991), are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments. The term "peptide" also includes chemically modified peptides, e.g., peptides containing modified amino acids or peptides which are, e.g., biotinylated, or are coupled to fluorophores, such as fluorescin, or Cy 3, are conformationally restricted, e.g. by disulfide bridging or by stapling (Walensky 2004, Science 305(5689): 1466-1470), or are linked to cell penetration peptides or protein transduction domains (Snyder 2004, Pharm Res 21(3): 389-393). Such modifications may improve the biological properties of the peptides, e.g., cell penetration, binding, stability, or may be used as detection labels. The peptide of the present invention can be recombinantly manufactured or may be chemically synthesised. The peptide may comprise further amino acids which may serve as a tag for purification or detection. Moreover, the peptide of the present invention may be comprised by a fusion polypeptide. The variant or modified peptides, preferably, retain the biological activity of the peptides having any one of SEQ ID NOs. 2 to 6, i.e. they are capable of inhibiting cell growth of HPV infected cells and/or induce apoptosis in said cells. These properties can be tested by the assays described in the accompanying Examples below.

Advantageously, the sequence motif comprised by the peptide of the present invention was found in accordance with the preset invention to be sufficient for specific and efficient binding of the peptide to the HPV E6 oncoprotein. Moreover, it was found that the peptides of the present invention are capable of selectively inhibiting cell growth of HPV infected cells and/or to induce apoptosis in said cells due to binding via the aforementioned sequence motif (SEQ ID NO: 1) to the HPV E6 oncoprotein.

In a preferred embodiment of the peptide of the present invention, said peptide further comprises a detectable tag. The term "detectable tag" refers to a stretch of amino acids which are added or introduced into the peptide of the invention. Preferably, the tag shall be added C- or N-terminally to the peptide of the present invention. The said stretch of amino acids shall allow for detection of the peptide by an antibody which specifically recognizes the tag or it shall allow for forming a functional conformation, such as a chelator or it shall allow for visualization by fluorescent tags. Preferred tags are the Myc-tag, FLAG-tag, 6-His-tag, HA-tag, GST-tag or GFP-tag. These tags are all well known in the art.

The present invention also relates to a fusion polypeptide comprising the peptide of the present invention. The term "fusion polypeptide" refers to a polypeptide comprising as a first entity the peptide of the present invention chemically linked to a second entity being a polypeptide or peptide. Preferably, the two entities of the fusion polypeptide are chemically linked via peptide bounds, i.e. forming a contiguous amino acid chain. However, the peptide of the present invention could also be linked via an amino acid side group to the polypeptide or peptide of the fusion polypeptide. Polypeptides or peptides fused to the peptide of the present invention are, preferably, polypeptides or peptides which support growth inhibition or which elicit apoptosis in HPV infected cells. Moreover, other polypeptides or peptides may allow for visualization of infected cells, such as fluorescent proteins (e.g., green, yellow, blue or red fluorescent proteins) or enzymes (e.g., firefly luciferase, alkaline phosphatase and the like). Other polypeptides or peptides are, preferably, antibodies or fragments thereof which allow for specifically targeting infected cells.

In a preferred embodiment of the polypeptide of the present invention, said fusion polypeptide further comprises an E6AP consensus motif, preferably as shown in SEQ ID NO: 9. Such an E6AP consensus sequence motif is to be found in the cellular E6AP protein, the cellular E6BP/ERC55 protein, tuberin or paxillin. The aforementioned proteins, preferably, are human proteins. Their sequence has been described in Huibregtse 1991, EMBO J. 10(13): 4129-35; Elston 1998, J Gen Virol 79(Pt2): 371-4; Be 2001, Biochemistry 40(5): 1293-9; Chen 1998, J Biol. Chem. 273(22): 13537-44, U.S. Pat. No. 5,914,389, U.S. Pat. No. 5,532,348, U.S. Pat. No. 6,296,853 (for E6AP), Chen 1995, Science 269(4893): 934-937, Elston 1998, J Gen Virol 79(Pt2): 371-374 (for E6BP/ERC55), Lu 2004, J Biol Chem 279(34): 35664-70 (for tuberin) or Tong 1997, J Biol Chem 272(52): 33373-6 (for paxillin). Also included in accordance with the present invention are variants such as paralogs or orthologs of the aforementioned human proteins. Such variants, preferably, have an amino acid sequence being at least 70%, at least 80%, at least 90%, at least 95%, at least 96%, at least 97%, at least 98% or at least 99% identical to the human E6AP protein. Thus, preferably, the fusion polypeptide may comprise the E6AP consensus sequence motif as a result of a fusion between any of the aforementioned proteins and the peptide of the present invention.

The present invention contemplates a polynucleotide encoding the peptide or the fusion polypeptide of the present invention.

The polynucleotide of the present invention, preferably, is a DNA or RNA molecule. The term encompasses single as well as double stranded polynucleotides. Moreover, comprised are also chemically modified polynucleotides including naturally occurring modified polynucleotides such as glycosylated or methylated polynucleotides or artificial modified one such as biotinylated polynucleotides. Based on the well known genetic code, polynucleotides encoding the peptide or fusion polypeptides of the present invention can be provided either by using mutagenesis approaches of naturally occurring nucleic acids or by chemical synthesis. The polynucleotide of the present invention encoding either the peptide or fusion polypeptide, preferably, comprises other nucleic acids as well. Such additional nucleic acids may be nucleic acids which are required for the governance of the expression of the peptide or fusion polypeptide or for its stability. More preferably, the polynucleotide will comprise an expression cassette for the peptide or fusion polynucleotide of the present invention. Such an expression cassette preferably comprises an expression control sequence operatively linked to the nucleic acid sequence encoding the peptide or fusion polypeptide as well as a transcription termination sequence downstream of the said coding sequence. Suitable expression control sequences or termination sequences are also referred to elsewhere in this specification.

The present invention also relates to a vector comprising the polynucleotide of the present invention.

The term "vector", preferably, encompasses phage, plasmid, viral or retroviral vectors as well artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, preferably, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing hosts or host cells.

More preferably, the vector of the invention is an expression vector wherein the polynucleotide of the present invention is operatively linked to expression control sequences allowing expression in prokaryotic or eukaryotic cells or isolated fractions thereof. Expression of said polynucleotide comprises transcription of the polynucleotide, preferably into a translatable mRNA. Regulatory elements ensuring expression in eukaryotic cells, preferably mammalian cells, are well known in the art. They, preferably, comprise regulatory sequences ensuring initiation of transcription and, optionally, poly-A signals ensuring termination of transcription and stabilization of the transcript. Additional regulatory elements may include transcriptional as well as translational enhancers. Possible regulatory elements permitting expression in prokaryotic host cells comprise, e.g., the lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (GIBCO BRL). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning A Laboratory Manual, Cold Spring Harbor Laboratory (1989) N.Y. and Ausubel, Current Protocols in Molecular Biology, Green Publishing Associates and Wiley Interscience, N.Y. (1994).

Further, the present invention relates to a host cell comprising the peptide, the fusion polypeptide, the polynucleotide or the vector of the present invention.

The term "host cell" refers to a prokaryotic or eukaryotic cell harbouring the peptide, fusion polypeptide, polynucleotide or vector of the present invention. It will be understood that prokaryotic cells may be used for propagation of polynucleotides encoding the peptide or fusion polynucleotide of the present invention or vectors comprising such polynucleotides while eukaryotic host cells such as HPV cell lines can be applied for testing the biological properties of the peptide, fusion polypeptide, polynucleotide or vector of the present invention. Preferably, prokaryotic host cells are bacteria and, preferably, *E. coli*. Eukaryotic host cells encompass all kinds of animal, plant or fungal cells and are, preferably, mammalian cells and, more preferably, human cells. Preferably, the eukaryotic host cells are transfected with the HPV. Preferred eukaryotic cells are also primary cells or cell lines derived from the neoplasia or tumors referred to herein.

The peptide, the fusion polypeptide, the polynucleotide, or the vector of the present invention is, in principle, applicable for use as a pharmaceutical composition. More specifically, they are used for treating or preventing HPV-associated neoplasia or tumors.

Accordingly, the present invention also includes the use of the peptide, fusion polypeptide, polynucleotide, or vector of the present invention for the manufacture of a pharmaceutical composition for treating or preventing HPV-associated neoplasia or tumors.

In particular, a method for treating or preventing HPV-associated neoplasia or tumors in a subject is provided in accordance with the present invention comprising administering to said subject a therapeutically effective amount of the peptide, the fusion polypeptide, the polynucleotide or the vector of the present invention.

The term "pharmaceutical composition" as used herein comprises the compounds of the present invention, i.e., the aforementioned peptide, fusion polypeptide, polynucleotide, or vector, and optionally one or more pharmaceutically acceptable carrier. The compounds of the present invention can be formulated as pharmaceutically acceptable salts. Acceptable salts comprise acetate, methylester, HCl, sulfate, chloride and the like. The pharmaceutical compositions are, preferably, administered topically or systemically. Suitable routes of administration conventionally used for drug administration are oral, intravenous, intravaginal, transmucosal, dermal or parenteral administration as well as inhalation. However, depending on the nature and mode of action of a compound, the pharmaceutical compositions may be administered by other routes as well. For example, polynucleotide compounds may be administered in a gene therapy approach by using viral vectors or viruses or liposomes.

Moreover, the compounds can be administered in combination with other drugs either in a common pharmaceutical composition or as separated pharmaceutical compositions wherein said separated pharmaceutical compositions may be provided in form of a kit of parts. Further, the pharmaceutical composition of the present invention can be applied in combination with other treatment options, such as surgery or radiation therapy.

The compounds are, preferably, administered in conventional dosage forms prepared by combining the drugs with standard pharmaceutical carriers according to conventional procedures. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables.

The carrier(s) must be acceptable in the sense of being compatible with the other ingredients of the formulation and being not deleterious to the recipient thereof. The pharmaceutical carrier employed may be, for example, either a solid, a gel or a liquid. Exemplary of solid carriers are lactose, terra alba, sucrose, talc, gelatin, agar, pectin, acacia, magnesium stearate, stearic acid and the like. Exemplary of liquid carriers are phosphate buffered saline solution, syrup, oil such as peanut oil and olive oil, water, emulsions, various types of wetting agents, sterile solutions and the like. Similarly, the carrier or diluent may include time delay material well known to the art, such as glyceryl mono-stearate or glyceryl distearate alone or with a wax. Said suitable carriers comprise those mentioned above and others well known in the art, see, e.g., Remington's Pharmaceutical Sciences, Mack Publishing Company, Easton, Pa.

The diluent(s) is/are selected so as not to affect the biological activity of the combination. Examples of such diluents are distilled water, physiological saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

A therapeutically effective dose refers to an amount of the compounds to be used in a pharmaceutical composition of the present invention which prevents, ameliorates or treats the symptoms accompanying a disease or condition referred to in this specification. Therapeutic efficacy and toxicity of such compounds can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50.

The dosage regimen will be determined by the attending physician and other clinical factors; preferably in accordance with any one of the above described methods. As is well known in the medical arts, dosages for any one patient depends upon many factors, including the patient's size, body surface area, age, the particular compound to be administered, sex, time and route of administration, general health, and other drugs being administered concurrently. Progress can be monitored by periodic assessment. A typical dose can be, for example, in the range of 1 to 1000 µg; however, doses below or above this exemplary range are envisioned, especially considering the aforementioned factors. Generally, the regimen as a regular administration of the pharmaceutical composition should be in the range of 1 µg to 10 mg units per day. If the regimen is a continuous infusion, it should also be in the range of 1 µg to 10 mg units per kilogram of body weight per minute, respectively. Progress can be monitored by periodic assessment. However, depending on the subject and the mode of administration, the quantity of substance administration may vary over a wide range to provide from about 0.01 mg per kg body mass to about 10 mg per kg body mass.

The pharmaceutical compositions and formulations referred to herein are administered at least once in order to treat or ameliorate or prevent a disease or condition recited in this specification. However, the said pharmaceutical compositions may be administered more than one time, for example from one to four times daily up to a non-limited number of days.

Specific pharmaceutical compositions are prepared in a manner well known in the pharmaceutical art and comprise at least one active compound referred to herein above in admixture or otherwise associated with a pharmaceutically acceptable carrier or diluent. For making those specific pharmaceutical compositions, the active compound(s) will usually be mixed with a carrier or the diluent, or enclosed or encapsulated in a capsule, sachet, cachet, paper or other suitable containers or vehicles. The resulting formulations are to be adapted to the mode of administration, i.e. in the forms of tablets, capsules, suppositories, solutions, suspensions or the like. Dosage recommendations shall be indicated in the prescribers or users instructions in order to anticipate dose adjustments depending on the considered recipient.

The term "treating" as used herein refers to ameliorating or curing the diseases or disorders referred to herein or at least the symptoms accompanied therewith. The said amelioration or cure may not occur in every subject which will be treated. However, it shall occur in a statistically significant portion of subjects of a population of subjects to be treated. Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population.

The term "preventing" as used herein means that the incidence of the diseases or disorders referred to herein or its symptoms will be prevented, preferably, within a defined time window starting from the preventive measure. It will be understood that after expiration of the said time window, a refreshment of the preventive measure may be required. The said prevention shall occur in a statistically significant portion of subjects of a population of subjects to be subjected to prevention. Whether a portion is statistically significant can be determined without further ado by the person skilled in the art using various well known statistic evaluation tools as described elsewhere in this specification.

The term "HPV-associated neoplasia or tumors" refers to neoplasia or tumors which occur a result of an HPV infection. Preferably, said HPV has a high risk HPV genotype, more preferably, HPV16, HPV18, HPV33, HPV45, HPV31, HPV58, HPV52, HPV35, or HPV59. The molecular characteristics of the high risk genotype and, in particular, those specifically mentioned before are well known to the person skilled in the art and are described, e.g., in Zur Hausen 2002, loc cit, or in Knipe 2006 Fields Virology, Lippincott Williams & Wilkins. Most preferably, HPV as used herein refers to HPV16. A preferred HPV-associated neoplasia or tumor in accordance with the present invention is a cervical neoplasia or tumor, anogenital warts (*Condylomata acuminata, Condylomata plana, Condylomata gigantea* (Buschke-Loewenstein tumor)), Cervical Intraepithelial Neoplasia, *Bowenoid papulosis* (*Bowenoid dysplasia*, viral keratosis), mucosa warts, larynx papilloma, malignant tumors, preferably, spinalioma accompanied with *Epidermodysplasia verruciformis*, Morbus Bowen of the skin, penis carcinoma, vulva carcinoma, squamous cell carcinoma of the skin, cervical carcinoma, larynx carcinoma, tonsillar carcinoma oropharynx or tongue carcinoma. The symptoms associated with the said diseases or disorders are well known in the art and described in detail in standard text books of medicine.

The peptide or the fusion polypeptide of the present invention is also, in principle, applicable for use as a diagnostic composition. More specifically, they are used for diagnosing HPV-associated neoplasia or tumors.

Accordingly, the present invention also relates to the use of the peptide or the polypeptide of the present invention for the manufacture of a diagnostic composition for diagnosing HPV-associated neoplasia or tumors.

Moreover, the present invention provides a method for diagnosing HPV-associated neoplasia or tumors in a subject comprising the steps of (a) contacting a sample of a subject suspected to suffer from HPV-associated neoplasia or tumors with a peptide or fusion polypeptide of the present invention and (b) determining binding of the HPV E6 protein to the said peptide or fusion polypeptide, thereby diagnosing the HPV-associated neoplasia or tumors.

The term "diagnosing" as used herein refers to assessing the probability according to which a subject is suffering or will suffer from a disease or condition referred to in this specification. As will be understood by those skilled in the art, such an assessment is usually not intended to be correct for 100% of the subjects to be diagnosed. The term, however, requires that a statistically significant portion of subjects can be correctly diagnosed to suffer from the disease or condition. Whether a portion is statistically significant can be determined without further ado by the person skilled in the art using various well known statistic evaluation tools as described elsewhere in this specification.

The present invention also refers to a method of identifying a compound capable of binding to the HPV E6 oncoprotein comprising:
  (a) contacting the HPV E6 oncoprotein with the peptide or the fusion polypeptide of the present invention and a compound suspected to be capable of binding to the HPV E6 protein; and
  (b) determining complex formation of the HPV E6 oncoprotein with the said peptide or the fusion polypeptide, whereby a decreased complex formation compared to a reference which has not been brought into contact with the compound is indicative for a compound capable of binding to the HPV E6 protein.

The term "compound capable of binding to the HPV E6 protein" refers to a small molecule, i.e. an organic substance, preferably, other than a peptide or polypeptide or inorganic chemical substance. The said compound shall be capable of binding to the HPV E6 oncoprotein. Preferably, the said binding shall interfere with the binding of the peptide or fusion polypeptide of the invention and the HPV E6 oncoprotein. Accordingly, the binding of the compound may physically block the binding site on the HPV E6 oncoprotein for the peptide or fusion polynucleotide or may allosterically alter the binding site whereby biding will be abolished. Suitable compounds may be obtained by screening of artificial chemical libraries obtained, e.g., by combinatorial chemistry approaches or by screening of natural compound libraries obtained, e.g., by fractioning extracts from biological organisms such as plants or animals. Suitable compounds can also be generated by in silico screening methods based on, e.g., molecular modelling approaches.

The term "contacting" as used herein may be carried out by mixing the components referred to in step a) in vitro. Alternatively, the term also relates to contacting a host cell comprising the HPV E6 oncoprotein and the peptide or fusion polypeptide of the invention with the compound to be tested. In the latter case, contacting requires to allow the compound to enter the host cells and to interact with the other components intracellularly. Suitable conditions can be adjusted by the skilled artisan without further ado.

Determining complex formation can be achieved directly by determining the amount of complexes formed between the peptide or fusion polypeptide of the present invention and the HPV E6 oncoprotein or indirectly by determining the amount of uncomplexed HPV E6 oncoprotein or the amount of the uncomplexed peptide or fusion polypeptide of the present invention. It will be understood that if the amount of the complex is determined, a decrease in the amount of the complex compared to the amount of complex found in a reference experiment wherein the HPV E6 oncoprotein, the peptide or the fusion polypeptide of the present invention have not been brought into contact with the compound suspected to be capable of binding to the HPV E6 protein will be indicative for a compound being capable of binding to the HPV E6 oncoprotein. Moreover, the amount of uncomplexed HPV E6 oncoprotein or the peptide or fusion polypeptide of the present invention will be increased compared to the corresponding amounts found in said reference experiment if the compound indeed is capable of binding to HPV E6 oncoprotein. The complex or the free HPV E6 oncoprotein, peptide or fusion polypeptide of the present invention can be, preferably, determined by antibodies which specifically recognize either the complex or any one of its components in uncomplexed form. The method, also preferably, comprises the additionally steps of determining the binding site of the compound on the HPV E6 oncoprotein. Suitable mapping approaches are well known in the art.

The present invention also relates to a kit comprising the peptide, the fusion polypeptide, the polynucleotide, the vector or the host cell of the present invention. Preferably, said kit is a diagnostic kit which can be applied to carry out the aforementioned diagnostic methods or a kit for identifying compounds capable of binding to the HPV E6 protein by applying a method as recited above.

The term "kit" as used herein refers to a collection of the compounds, means or reagents of which may or may not be packaged together. The components of the kit may be comprised by separate vials (i.e. as a kit of separate parts) or provided in a single vial. Moreover, it is to be understood that the kit of the present invention is to be used for practicing the methods referred to herein above. It is, preferably, envisaged that all components are provided in a ready-to-use manner for practicing the methods referred to above. Further, the kit preferably contains instructions for carrying out the said methods. The instructions can be provided by a users manual in paper- or electronic form. For example, the manual may comprise instructions for interpreting the results obtained when carrying out the aforementioned methods using the kit of the present invention.

The figures show:

FIG. 1: a) 5'-3' sequences of identified active peptides which bind to the HPV16 E6 oncoprotein. E6 pep 1 (a1, SEQ ID NO: 2), E6 pep5 (a2, SEQ ID NO: 3), and E6 pep 11 (a3, SEQ ID NO: 4) were identified by yeast two-hybrid screening. E6 pep 11* (a4, SEQ ID NO: 5) and E6 pep 11** (a5, SEQ ID NO: 6) are two solubility-optimized versions of E6 pep 11. Mutational studies revealed a conserved sequence motif required for binding to HPV16 E6. b) Two inactive peptides, pep 11*m (b 1, SEQ ID NO: 7) and pep11**m (b2, SEQ ID NO: 8), are shown exemplary. c) and d) show the sequence motif of active peptides (SEQ ID NO: 1) and the E6AP consensus motif (SEQ ID NO: 9), respectively. h hydrophobic amino acid (e.g. W, I, L or V); x any amino acid;

b hydrogen bound generating amino acid (e.g., D, E, Q); a acidic amino acid (e.g., E or D); s small amino acid (e.g., A or G).

FIG. 2: Binding studies in mammalian cells employing the CheckMate™ mammalian two-hybrid system. HeLa cells were co-transfected with expression vectors for HPV16 E6/GAL4 DB (binding domain fusion), peptides/VP16AD (activation domain fusion), and the luciferase reporter construct pG5luc. Fold activation values represent luciferase activities above the empty AD vector (pACT2). E6AP refers to the E6 binding consensus motif within E6AP. n=3–/+SD.

Figure 3:
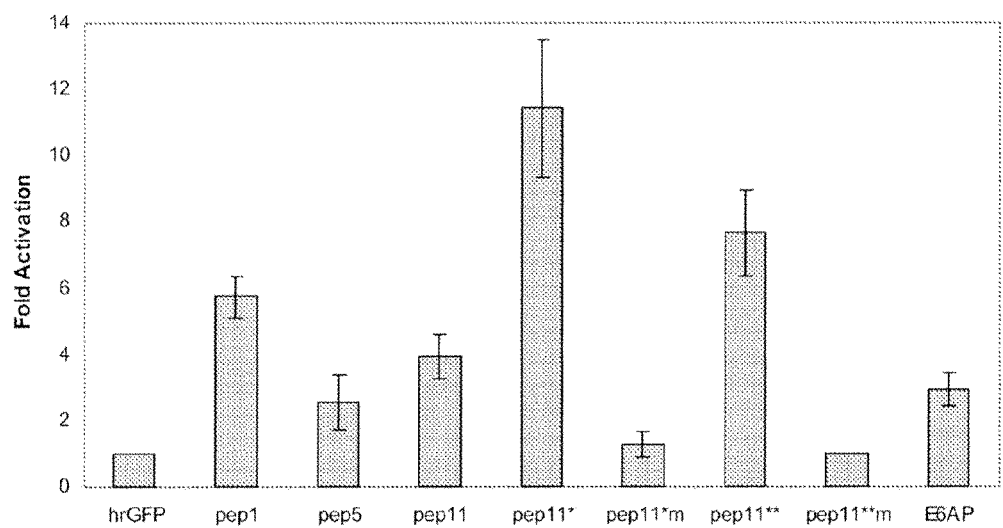

FIG. 3: Reactivation of p53 by pep 11 in HPV16-positive MRI-H-186 cells. Cells were co-transfected with peptide expression vectors and a p53-responsive luciferase reporter construct. Luciferase activity of the empty vector (hrGFP) was set at 1.0. n=3–/+SD.

Figure 4:
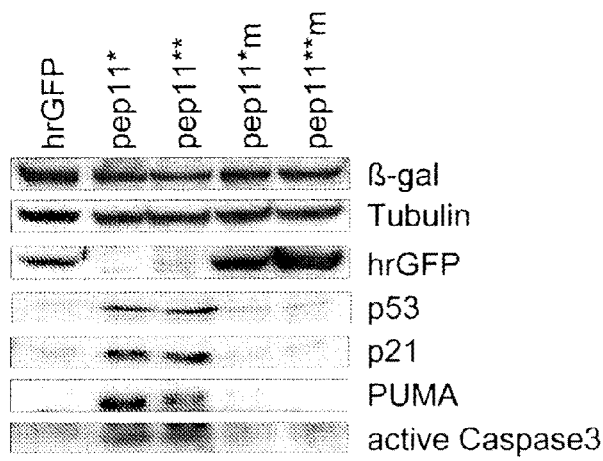
Figure 4:
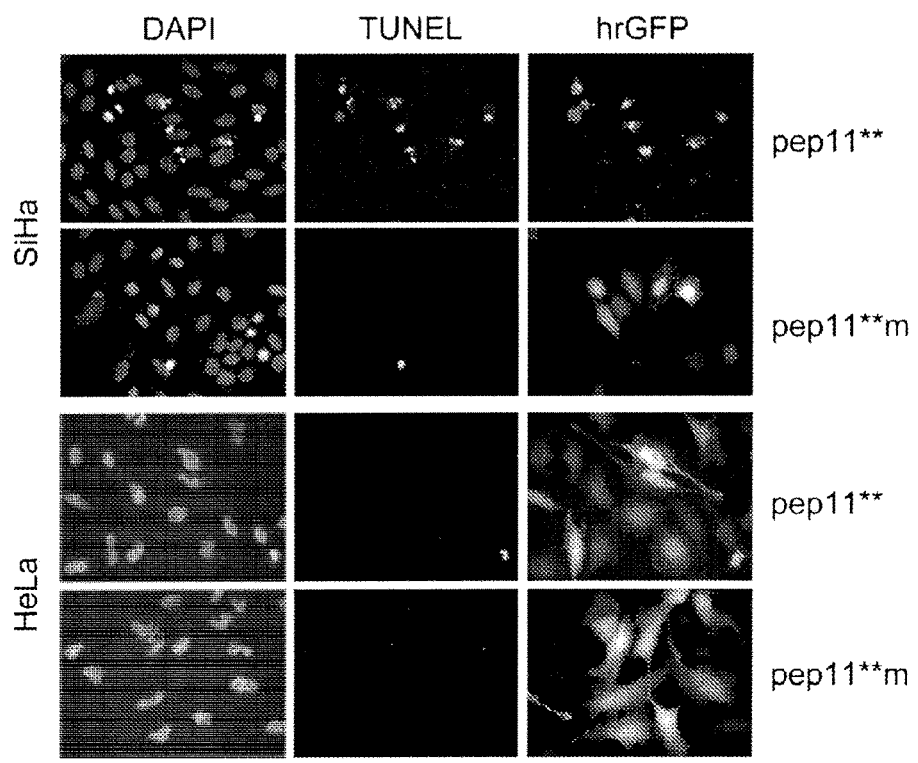

FIG. 4: Pep11 selectively induced apoptosis in HPV16-positive cells. (A) Expression of active pep 11 variants as hrGFP fusion proteins in HPV 16-positive SiHa cells led to an increased expression of p53, p53 targets (p21, PUMA), and apoptotic markers (active Caspase 3). Inactive mutants had no effect. β-Gal, transfection control. (B) Expression of pep11** as hrGFP fusion protein induced apoptosis in HPV16-positive SiHa cells. HPV18-positive control cells (HeLa) remained unaffected.

Figure 5:
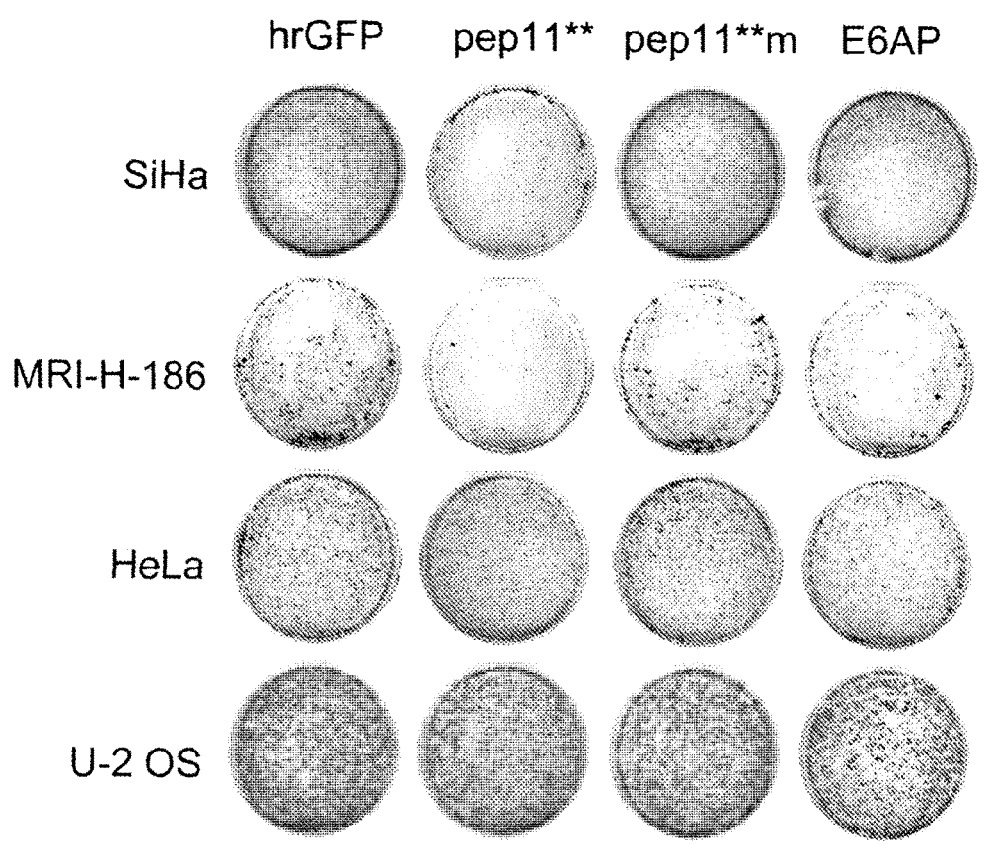

FIG. 5: Stable expression of pep11 inhibited the growth of HPV16-positive cell lines (SiHa, CaSki) in clonogenic survival assays, but not of HPV18-positive cells (HeLa), or HPV negative cells (U-2 OS). A non-binding mutant pep 11m and the E6AP peptide showed no effect.

The following Examples illustrate the invention. The Examples shall, whatsoever, not be construed as limiting the scope of the invention.

EXAMPLE 1

Screening for HPV-E6 Binding Peptides

The approach used was derived from the peptide aptamer system (Hoppe-Seyler 2004, Curr Mol Med 4(5): 529-538). To identify HPV-E6 binding peptides, a randomized oligopeptide expression library was established for 20 amino acid-long, linear peptides. Codons were defined by the sequence NNK (N=G, A, T or C; K=G or C). They code for all of the 20 amino acids, but only result in one stop codon. The peptides were expressed as GAL4AD fusions in the yeast expression vector pADpep. The yeast strain KF-1 (Butz 2000, Proc. Natl. Acad. Sci. USA 97(12): 6693-7) contained three nutritional selection markers: ADE2, HIS3 and URA3, each of them under the transcriptional control of GAL4 binding sites on the basis of various promoters. The URA3 selection marker was regulated by the SPO13 promoter which contained a negatively regulatory element and could be activated only by strong protein-protein interactions (Vidal 1996, Proc. Natl. Acad. Sci. USA 93(19): 10315-20). The HPV16 E6 protein, expressed from the yeast expression vector pPC97 (Vidal 1996 loc cit), was subjected to screening using the ADE2 marker of the system described above. Clones which activated at least the HIS3 and the ADE2 marker were analysed further, the corresponding peptide expression plasmids were isolated and re-transformed and re-screened in yeast which confirmed initial in vivo binding activities.

Sequence analysis of the isolated peptide plasmids revealed 6 different peptide sequences. Three of those peptides contained a novel, conserved amino acid motif (FIG. 1) with no homology to known human proteins. Four of the peptides showed sequence homologies to the E6 binding motif present in E6AP and other proteins (Chen 1998, J Biol Chem 272(22): 13537-44), two of them containing the novel motif and the E6AP consensus sequence adjacent to another. One peptide showed no similarity to any of the two binding motifs.

To further analyse the in vivo binding behaviour in yeast, pPC97 expression vectors coding for E6 proteins of different HPV types were employed, in particular HPV16, HPV18, HPV6, and HPV11. Peptides displaying the novel binding motif selectively interacted with the E6 oncoprotein of HPV16 and not with other HPV types tested.

EXAMPLE 2

Binding Analysis in Mammalian Cells

Peptide-protein interactions in mammalian cells were investigated by employing the CheckMate™ Mammalian Two-Hybrid system (Promega, Mannheim, Germany). The HPV16 E6 coding sequence was fused to the GAL4-DNA binding domain (pBIND2 vector), and peptide sequences were expressed in fusion with the activation domain of herpes simplex virus type 1 VP16 (pACT2 vector). Both pBIND2- and pACT2 fusion constructs were transfected as duplicates into HeLa cells along with pG5luc, a plasmid containing five GAL4 binding sites upstream of a minimal TATA box upstream of the firefly luciferase gene, and the internal standard pCMV-Gal (Butz 1993, J Viol 67(11): 6476-6486), to correct for transfection efficacy. Two days after transfection, luciferase activities were quantified and corrected for variations in transfection efficacies, as determined by β-galactosidase activities.

EXAMPLE 3

Reactivation of Endogenous p53 in HPV16-Positive Cells

Peptides were expressed as hrGFP (human recombinant green fluorescent protein, Stratagene, Heidelberg, Germany) fusion constructs in HPV16-positive MRI-H-186 cells, along with a p53-responsive luciferase reporter construct and the internal standard pCMV-Gal (Butz 1993, loc cit). Two days after transfection, luciferase activities were quantified and corrected for variations in transfection efficacies, as determined by β-galactosidase activities.

EXAMPLE 4

Apoptosis Induction Upon pep11 Expression in HPV16-Positive Cells (A) Peptide variants and inactive peptide mutants were expressed as hrGFP fusions in HPV16-positive SiHa cells, along with pCMV-Gal as transfection control. Protein levels of p53, p53 target proteins (p21, PUMA) and the apoptosis marker active Caspase-3 were investigated by western blot analysis. Tubulin served as a loading control.

(B) Pep11 or the inactive mutant pep11m were expressed as hrGFP fusion proteins in HPV16-positive SiHa cells or a control cell line (HPV18-positive HeLa). Cells grown on coverslips were fixed, stained with DAPI (4',6-diamidino-2-phenylindole) and labelled for apoptotic strand breaks with TUNEL (Tdt-mediated dUTP nick end labelling). Nuclei, TUNEL signals and hrGFP fluorescence were visualized by epifluorescence microscopy.

EXAMPLE 5

Clonogenic Survival Assay in HPV16-Positive Cell Lines and Control Cell Lines HPV16-positive cell lines SiHa and MRI-H-186, HPV18-positive HeLa cells and the HPV-negative osteosarcoma cell line U-2 OS were transfected with peptide expression vectors which allowed for hygromcyin B selection (pCEP4, Invitrogen). After 6-7 days of selection, cells were fixed and stained with formaldehyde-crystal violet solution.

In summary, peptides according to the invention inhibit the anti-apoptotic activity of HPV-E6 proteins, leading to apoptosis induction and growth arrest. Peptides according to the invention are suited to selectively eliminate HPV-positive cells, in particular HPV tumor cells.

The invention claimed is:

1. A peptide comprising an amino acid sequence motif as shown in SEQ ID No: 1, wherein the peptide further comprises the sequence of any one of SEQ ID NOs: 2-6 or variants thereof, and wherein the variants have an amino acid sequence that is at least 70% identical to the amino acid sequence shown in any one of SEQ ID NOs: 2-6.

2. The peptide of claim 1, wherein said peptide consists of up to 30 amino acids.

3. The peptide of claim 1, wherein said peptide comprises an amino acid sequence as shown in any one of SEQ ID Nos: 2 to 6.

4. The peptide of claim 1, wherein said peptide further comprises a detectable tag.

5. The peptide of claim 1, comprised in a fusion polypeptide.

6. A peptide comprising an amino acid sequence motif as shown in SEQ ID NO: 1, wherein the peptide is comprised in a fusion polypeptide also comprising an E6AP consensus sequence motif.

7. The peptide of claim 1, for use as a pharmaceutical composition.

8. The peptide of claim 1, to be used for treating HPV-associated neoplasia or tumors.

9. The peptide of claim 1, for use as a diagnostic composition.

10. The peptide of claim 1, to be used for diagnosing HPV-associated neoplasia or tumors.

11. The peptide of claim 8, wherein said HPV-associated neoplasia or tumor is selected from the group consisting of a cervical neoplasia or tumor, anogenital warts, *Condylomata acuminata, Condylomata plana, Condylomata gigantea* (Buschke-Loewenstein tumor), Cervical Intraepithelial Neoplasia, *Bowenoid papulosis* (*Bowenoid dysplasia*, viral keratosis), mucosa warts, larynx papilloma and malignant tumors.

12. The peptide of claim 8, wherein said HPV is HPV 16.

13. A kit comprising the peptide of claim 1.

14. A method of identifying a compound capable of binding to the HPV E6 protein comprising:
(a) contacting the HPV E6 protein with the peptide of claim 1, and a compound suspected to be capable of binding to the HPV E6 protein; and
(b) determining complex formation of the HPV E6 protein with the peptide of claim 1, whereby a decreased complex formation compared to a reference which has not been brought into contact with the compound is indicative for a compound capable of binding to the HPV E6 protein.

15. A method for treating HPV-associated neoplasia or tumors in a subject comprising administering to said subject a therapeutically effective amount of the peptide of claim 1.

16. The method of claim 15, wherein said HPV-associated neoplasia or tumor is a cervical neoplasia or tumor, anogenital warts (*Condylomata acuminata, Condylomata plana, Condylomata gigantea* (Buschke-Loewenstein tumor)), Cervical Intraepithelial Neoplasia, *Bowenoid papulosis* (*Bowenoid dysplasia*, viral keratosis), mucosa warts, larynx papilloma, malignant tumors, spinalioma accompanied with *Epidermodysplasia verruciformis*, Morbus Bowen of the skin, penis carcinoma, vulva carcinoma, squamous cell carcinoma of the skin, cervical carcinoma, larynx carcinoma, tonsillar carcinoma, oropharynx or tongue carcinoma.

17. The method of claim 15, wherein said HPV is HPV 16.

18. A host cell comprising the peptide of claim 1.

19. The peptide of claim 11, wherein said HPV-associated neoplasia or tumor is a malignant tumor selected from the group consisting of spinalioma accompanied with *Epidermodysplasia verruciformis*, Morbus Bowen of the skin, penis carcinoma, vulva carcinoma, squamous cell carcinoma of the skin, cervical carcinoma, larynx carcinoma, tonsillar carcinoma, oropharynx carcinoma, and tongue carcinoma.

* * * * *

UNITED STATES PATENT AND TRADEMARK OFFICE
CERTIFICATE OF CORRECTION

PATENT NO. : 8,598,126 B2  Page 1 of 1
APPLICATION NO. : 12/936679
DATED : December 3, 2013
INVENTOR(S) : Hoppe-Seyler et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 309 days.

Signed and Sealed this
Twenty-first Day of April, 2015

Michelle K. Lee
*Director of the United States Patent and Trademark Office*

```
                        SEQUENCE LISTING

<160> NUMBER OF SEQ ID NOS: 10

<210> SEQ ID NO 1
<211> LENGTH: 10
<212> TYPE: PRT
<213> ORGANISM: artificial
<220> FEATURE:
<223> OTHER INFORMATION: consensus sequence
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(4)
<223> OTHER INFORMATION: hydrophobic amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (7)..(7)
<223> OTHER INFORMATION: hydrophobic amino acid
<220> FEATURE:
<221> NAME/KEY: MISC_FEATURE
<222> LOCATION: (8)..(10)
<223> OTHER INFORMATION: any amino acid

<400> SEQUENCE: 1

Cys Xaa Cys Xaa Xaa Cys Xaa Xaa Xaa Xaa
1               5                   10

<210> SEQ ID NO 2
<211> LENGTH: 22
<212> TYPE: PRT
<213> ORGANISM: artificial
<220> FEATURE:
<223> OTHER INFORMATION: E6 pep1

<400> SEQUENCE: 2

Lys Gly Ser Leu Asn Cys Ser Cys Leu Val Cys Trp Leu Gln Met Phe
1               5                   10                  15

Leu Gly Glu Phe Gly Pro
            20

<210> SEQ ID NO 3
<211> LENGTH: 22
<212> TYPE: PRT
<213> ORGANISM: artificial
<220> FEATURE:
<223> OTHER INFORMATION: E6 pep5

<400> SEQUENCE: 3

Pro Phe Leu Leu Gly Cys Phe Cys Leu Cys Cys Trp Ile Glu Cys Gln
1               5                   10                  15

Ile Gly Ser Tyr Gly Pro
            20
```

```
<210> SEQ ID NO 4
<211> LENGTH: 15
<212> TYPE: PRT
<213> ORGANISM: artificial
<220> FEATURE:
<223> OTHER INFORMATION: E6 pep11

<400> SEQUENCE: 4

Glu Phe Gly Ser Gly Cys Ser Cys Ile Val Cys Ile Gly Leu Ile
1               5                   10                  15

<210> SEQ ID NO 5
<211> LENGTH: 15
<212> TYPE: PRT
<213> ORGANISM: artificial
<220> FEATURE:
<223> OTHER INFORMATION: E6 pep11*

<400> SEQUENCE: 5

Glu Tyr Asn Ser Asn Cys Ser Cys Ile Ala Cys Ile Gly Leu Ile
1               5                   10                  15

<210> SEQ ID NO 6
<211> LENGTH: 19
<212> TYPE: PRT
<213> ORGANISM: artificial
<220> FEATURE:
<223> OTHER INFORMATION: E6 pep11**

<400> SEQUENCE: 6

Lys Glu Lys Glu Glu Tyr Asn Ser Asn Cys Ser Cys Ile Ala Cys Ile
1               5                   10                  15

Gly Leu Ile

<210> SEQ ID NO 7
<211> LENGTH: 15
<212> TYPE: PRT
<213> ORGANISM: artificial
<220> FEATURE:
<223> OTHER INFORMATION: E6 pep11*

<400> SEQUENCE: 7

Glu Tyr Asn Ser Asn Cys Ser Cys Ile Ala Cys Ile Gly Leu Ile
1               5                   10                  15

<210> SEQ ID NO 8
<211> LENGTH: 15
<212> TYPE: PRT
<213> ORGANISM: artificial
<220> FEATURE:
<223> OTHER INFORMATION: E6 pep11*

<400> SEQUENCE: 8

Glu Tyr Asn Ser Asn Cys Ser Cys Ile Ala Cys Ile Gly Leu Ile
1               5                   10                  15

<210> SEQ ID NO 9
<211> LENGTH: 19
<212> TYPE: PRT
<213> ORGANISM: artificial
<220> FEATURE:
<223> OTHER INFORMATION: E6 pep11*

<400> SEQUENCE: 9

Lys Glu Lys Glu Glu Tyr Asn Ser Asn Ser Ser Ser Ile Ala Ser Ile
1               5                   10                  15
```

```
Gly Leu Ile

<210> SEQ ID NO 10
<211> LENGTH: 7
<212> TYPE: PRT
<213> ORGANISM: artificial
<220> FEATURE:
<223> OTHER INFORMATION: E6 pep11*
<220> FEATURE:
<221> NAME/KEY: MISC_FEATURE
<222> LOCATION: (2)..(2)
<223> OTHER INFORMATION: basic amino acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: hydrophobic amino acid
<220> FEATURE:
<221> NAME/KEY: MISC_FEATURE
<222> LOCATION: (6)..(6)
<223> OTHER INFORMATION: small amino acid
<220> FEATURE:
<221> NAME/KEY: MISC_FEATURE
<222> LOCATION: (7)..(7)
<223> OTHER INFORMATION: acidic amino acid

<400> SEQUENCE: 10

Lys Xaa Xaa Xaa Lys Xaa Xaa
1               5
```